United States Patent
Adams

(10) Patent No.: US 6,171,300 B1
(45) Date of Patent: Jan. 9, 2001

(54) TUBING CASSETTE AND METHOD FOR COOLING A SURGICAL HANDPIECE

(75) Inventor: Kenneth M. Adams, Tampa, FL (US)

(73) Assignee: Linvatec Corporation, Largo, FL (US)

( * ) Notice: Under 35 U.S.C. 154(b), the term of this patent shall be extended for 0 days.

(21) Appl. No.: 09/140,133

(22) Filed: Aug. 25, 1998

Related U.S. Application Data

(60) Provisional application No. 60/057,927, filed on Sep. 4, 1997.

(51) Int. Cl.[7] .................................................. A61B 1/08
(52) U.S. Cl. .................... 606/1; 606/80; 604/35; 433/104
(58) Field of Search .................... 606/1, 20, 21, 606/22, 23, 80, 178, 179, 180; 604/19, 35, 173; 433/82, 104, 119, 126, 132, 128; 408/66; 451/488; 30/123.3; 83/170, 171

(56) References Cited

U.S. PATENT DOCUMENTS

| | | |
|---|---|---|
| 3,173,207 | 3/1965 | Burzlaff . |
| 3,324,552 | 6/1967 | Saffir . |
| 4,007,529 * | 2/1977 | Fleer ..................................... 433/104 |
| 4,107,846 | 8/1978 | Fleer et al. . |
| 4,184,256 | 1/1980 | Loge et al. . |
| 4,219,618 * | 8/1980 | Leonard ................................. 433/80 |
| 4,370,131 * | 1/1983 | Banko ..................................... 433/86 |
| 4,428,748 | 1/1984 | Peyman et al. . |
| 4,490,113 | 12/1984 | Kawada . |
| 4,505,676 * | 3/1985 | Gonser ................................. 433/119 |
| 4,547,687 * | 10/1985 | Arai ....................................... 310/58 |
| 4,568,283 * | 2/1986 | Hotta et al. .......................... 433/104 |
| 4,802,852 | 2/1989 | Shea . |
| 5,078,605 | 1/1992 | Sutter et al. . |
| 5,318,433 | 6/1994 | Overmyer . |
| 5,405,348 | 4/1995 | Anspach, Jr. et al. . |
| 5,571,106 | 11/1996 | Coufal et al. . |
| 5,613,812 | 3/1997 | Levan et al. . |
| 6,007,556 * | 12/1999 | Kablik et al. ........................ 606/180 |

* cited by examiner

*Primary Examiner*—Linda C. M. Dvorak
*Assistant Examiner*—David M. Ruddy
(74) *Attorney, Agent, or Firm*—Gene Warzecha

(57) ABSTRACT

A tubing cassette and method for use in cooling a surgical handpiece. The handpiece is provided with a drive motor which is received within a cooling chamber adapted to circulate cooling fluid around the motor. The cooling chamber is accessible from the exterior of the handpiece via inflow and outflow apertures, and a disposable cassette is selectively attachable to the exterior of the handpiece so as to communicate inflow and outflow apertures of the cassette with the inflow and outflow apertures on the handpiece body. The cassette is provided with inflow and outflow ports in communication with its inflow and outflow apertures in order to direct cooling fluid into and out of the cooling chamber via tubes through which coolant fluid may be circulated with the aid of an external pump, if desired.

6 Claims, 4 Drawing Sheets

TUBING CASSETTE AND METHOD FOR COOLING A SURGICAL HANDPIECE

Priority for this application is based on previously filed, copending provisional application No. 60/057,927, filed Sep. 4, 1997

BACKGROUND OF THE INVENTION

1. Field of the Invention

The invention relates generally to powered surgical instruments. More particularly, the invention relates to high speed electrically operated surgical instruments such as drills, etc. and devices for cooling such instruments.

2. Description of the Prior Art

The use of high speed electric motors in handpieces in medical applications raises a concern for controlling the temperature of the handheld devices operated by these motors. The present invention is directed to maintaining the temperature of such devices within acceptable limits by using cooling fluid.

High speed electric motors are known to be used in surgical orthopedic applications but, because they are generally used for shorter surgical procedures, temperature buildup has not been a significant issue. High speed motors intended to be used for extended periods of time are currently powered by pneumatic means because the expansion of gases used to drive these motors provides cooling to maintain the handheld device at acceptable temperatures.

Device size and logistical constraints (e.g. availability of fluids to power pneumatic devices) have created a need for the use of smaller, more practical electric devices rather than pneumatic devices. While the necessity to control the temperature of these devices is the subject of this invention, an added feature is that the fluid used to cool the motor may also be used to irrigate the surgical site, thereby eliminating the need for a separate irrigation source.

Additionally, in surgical procedures performed with handheld powered instruments it is necessary to sterilize the instruments prior to use. Therefore, in order to enable a high speed electric handpiece to be used, the handpiece must be provided with a cooling mechanism which does not compromise the sterilizability of the instrument. Some prior art dental device patents are known which are related to this problem, but the devices taught by these patents may be difficult to clean and sterilize.

The use of cooling water is shown in U.S. Pat. No. 3,324,552 (Saffir) in a dental handpiece having a removable electric motor. The water is circulated in a chamber around the outside of the motor and may be partially directed to flush the area of the tooth being drilled or cool the burr or other tool being used. However, the Saffir device may be difficult to clean and since surgical handpieces must be sterilized after use, it would be preferable to be able to detach and discard any coolant tubing prior to cleaning and sterilizing the handpiece.

U.S. Pat. No. 4,184,256 (Loge et al.)shows a dental handpiece having a coolant line in the motor thereof and U.S. Pat. No. 4,107,846 (Fleer et al.) shows a dental handpiece having a flexible hose which may be plugged into a pair of conduits to direct coolant to the dental tool being use. However, no known prior art shows a surgical handpiece adapted to be cooled via a disposable tubing set easily attachable to the handpiece.

It is accordingly an object of this invention to provide a surgical handpiece which may be cooled by circulating fluid.

It is also an object of this invention to provide a fluid cooled surgical handpiece operable with a tubing set which may be discarded after a single use.

It is another object of this invention to provide such a fluid cooled surgical handpiece with a tubing set having a cassette which facilitates selective attachment of the tubing set to the handpiece.

SUMMARY OF THE INVENTION

These and other objects of the invention are achieved by the preferred embodiment disclosed herein which is a fluid-cooled surgical handpiece system for use with a coolant source and coolant drain. The system comprises a handpiece and a tubing set, the handpiece comprising a body having a drive motor and a cooling chamber surrounding the motor. The handpiece also comprises a first inflow aperture for receiving the coolant from the coolant source and directing it to the chamber, and a first outflow aperture for directing the coolant from the chamber to the coolant drain. The system further comprises a tubing set for being engaged with the handpiece and for simultaneously engaging the inflow and outflow apertures and connecting them in fluid communication to the coolant source and the coolant drain, respectively.

DESCRIPTION OF THE PREFERRED EMBODIMENT

Figure 1:
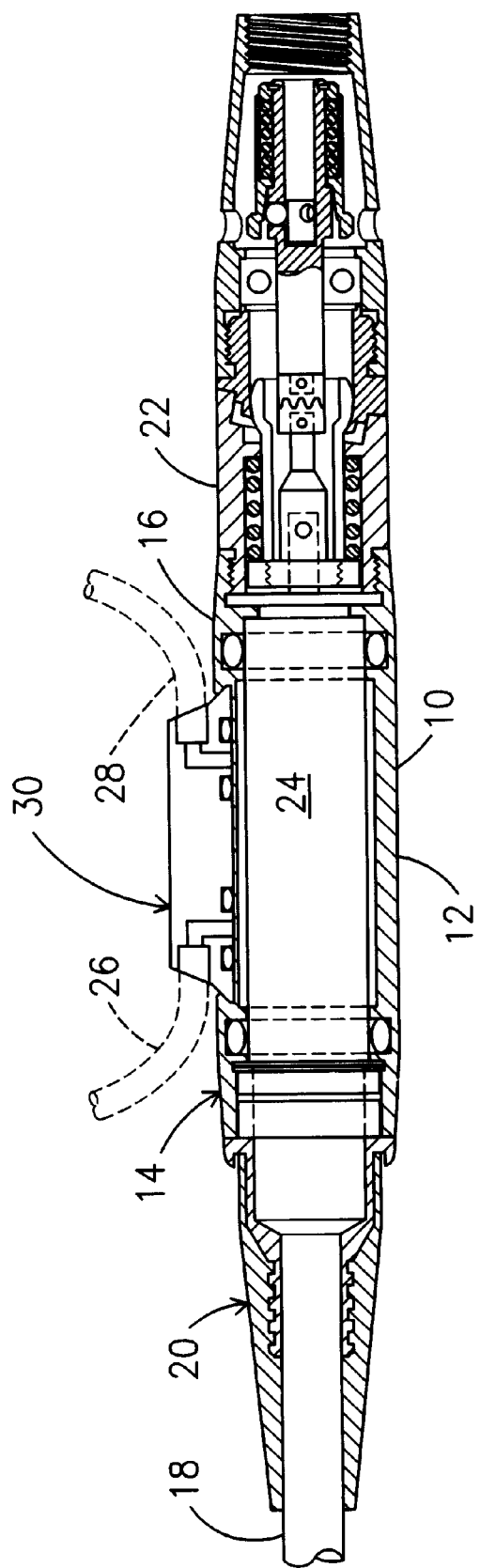
FIG. 1 is a side elevation view in cross-section of a surgical handpiece constructed in accordance with the principles of this invention.

FIG. 1 shows an electric powered surgical handpiece constructed in accordance with the principles of this invention. Handpiece 10 comprises a body 12 having a proximal end 14 and a distal end 16. Attached to proximal end 14 is electric cable 18 and a strain relief 20, both of which are used in a conventional matter. Attached to distal end 16 is a collet mechanism 22 adapted to receive a burr or drill (not shown) for use during a surgical procedure. Within body 12 is a chamber 24 for housing an electric motor (not shown) in such a way that the area surrounding the electric motor comprises a cooling chamber which may have a cooling fluid circulated therethrough. An irrigation cassette 30 is attached to the exterior of handpiece 10 adjacent to cooling chamber 24. As will be understood below, cassette 30 is intended to be used with flexible inlet and outlet tubes 26 and 28 for conveying to the handpiece a cooling fluid from a fluid coolant source (not shown) and directing spent fluid to a drain or other outflow receptacle. Preferably an external pump (not shown) is used to enhance fluid flow (e.g. sterile saline or water).

Figure 3:
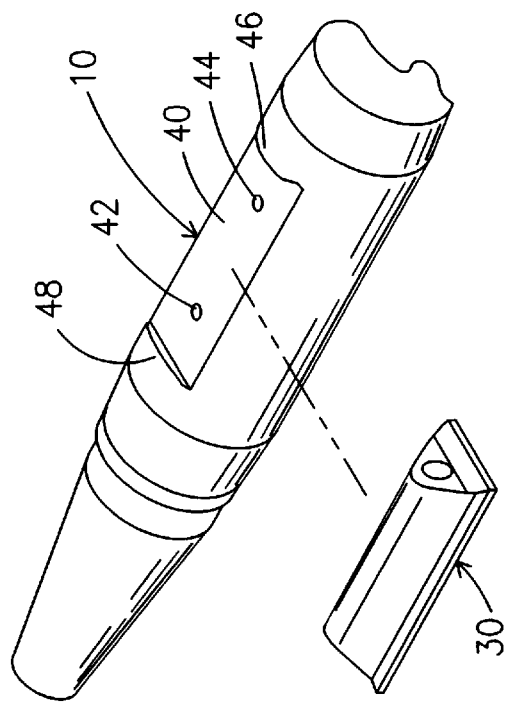
FIG. 3 is a front perspective view of the device of FIG. 1 showing the manner in which the cassette portion of the tubing set may be attached to the handpiece.
Figure 4:
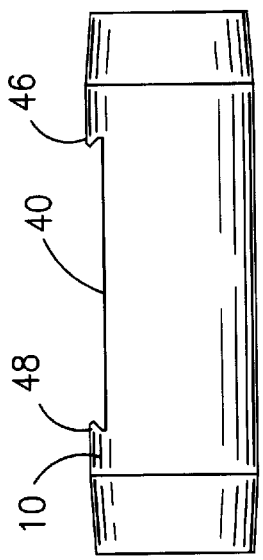
FIG. 4 is a side elevational view of the body of the surgical handpiece shown in FIG. 3.
Figure 2:
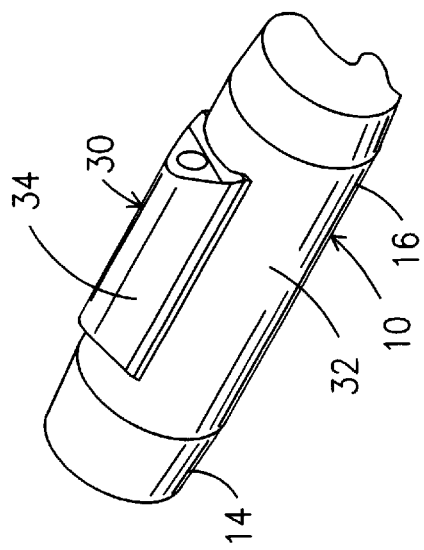
FIG. 2 is a front perspective view of a portion of the device of FIG. 1.

As shown in FIG. 2, handpiece 10 and irrigation cassette 30 have external surfaces 32 and 34, respectively, which are designed to smoothly blend with each other to produce a comfortable fit for the operating surgeon. It will be understood that the cassette and handpiece body could be joined in many other ways. For example, the cassette could have a cylindrical or semi-cylindrical clip resiliently conforming to the cylindrical handpiece body. As shown in FIG. 3, in the preferred embodiment irrigation cassette 30 is adapted to slide onto body 10 so as to be placed adjacent a surface 40 formed on the exterior of body 10 and provided with an inlet aperture 42 and an outlet aperture 44. It will be understood that fluid may flow through the chamber in opposite directions so the inlet and outlet could be reversed. As best seen in FIG. 4, surface 40 is bounded at its proximal and distal ends with arcuate projections 46 and 48 which provide a dovetail fit for retaining irrigation cassette 30 adjacent surface 40.

Figure 7:
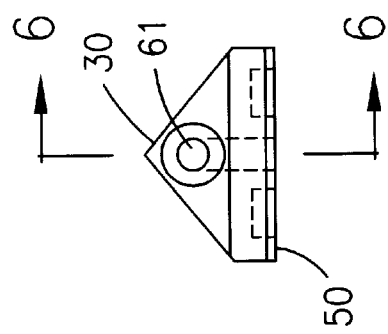
FIG. 7 is a right side view of FIG. 5.
Figure 5:
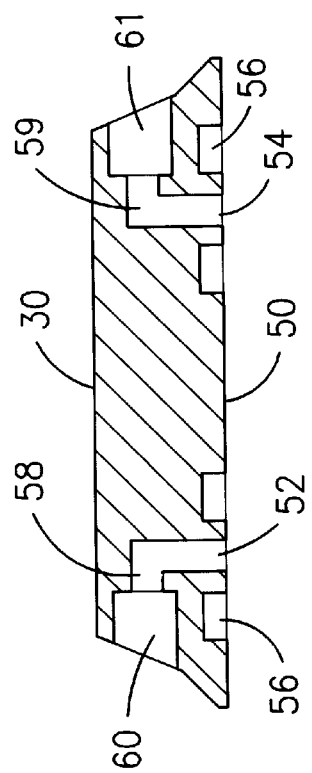
FIG. 5 is a side elevational view of the cassette portion of the tubing set shown in FIG. 3, in cross-section.
Figure 6:
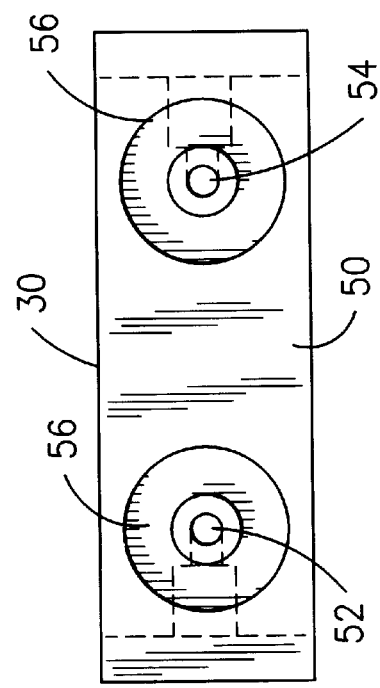
FIG. 6 is a bottom plan view of FIG. 5.

As shown in FIGS. 5 through 7, irrigation cassette 30 has a bottom surface 50 provided with inlet and outlet apertures 52 and 54, respectively. Each aperture is surrounded by an O-ring receiving groove 56 for receiving O-rings (not shown) to seal the area. Surface 50 is adapted to be engaged with surface 40 in such a way that fluid communication may be selectively and simultaneously established between inlet apertures 42 and 52, and outlet apertures 44 and 54. Within the body of irrigation cassette 30, inlet and outlet apertures 52 and 54 communicate with conduits 58 and 59, respectively, which in turn communicate with inlet and outlet ports 60 and 61, respectively, to which tubes 26 and 28 (FIG. 1) are connected. The orientation of the conduits and ports in the cassette may be changed to accommodate various tubing set configurations.

Figure 8:
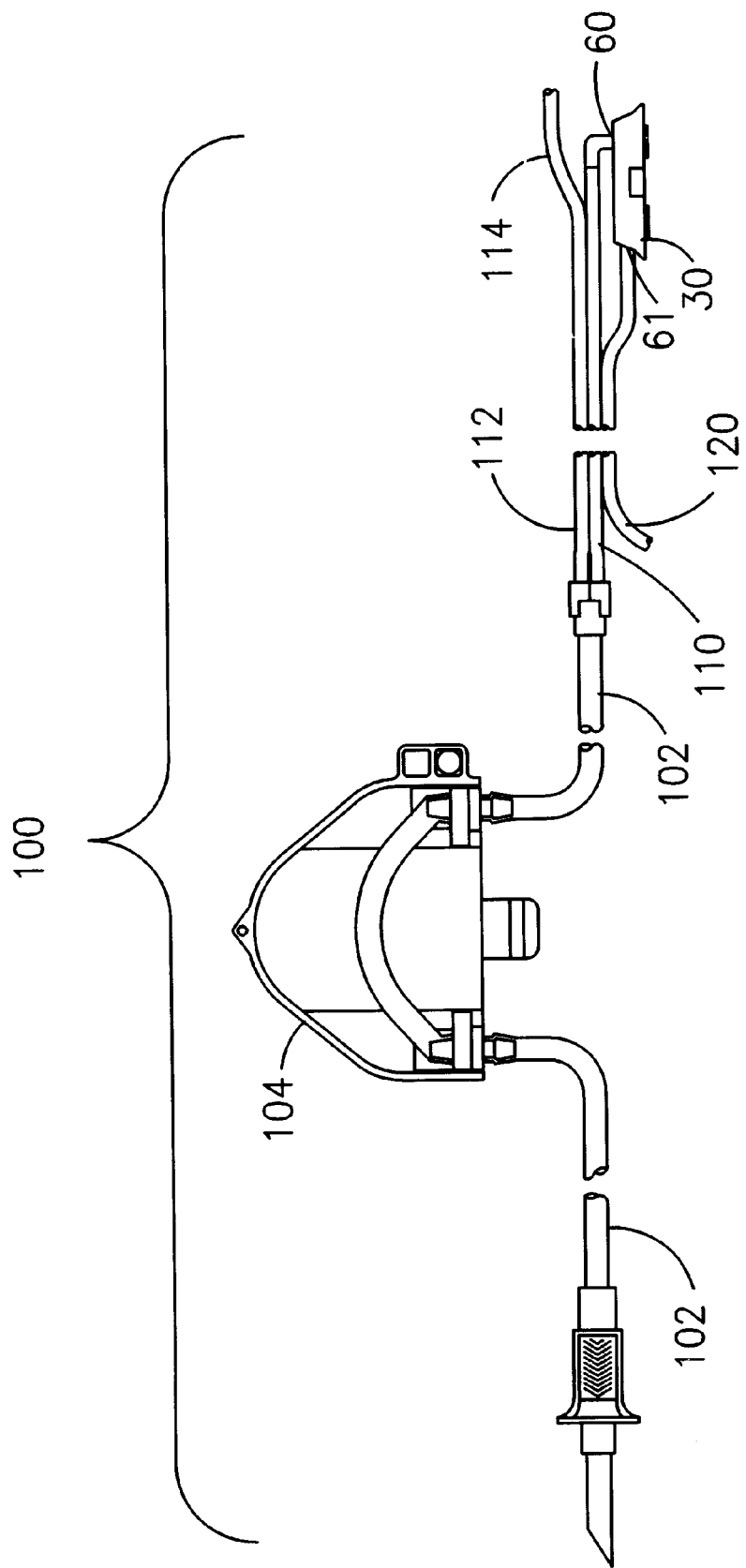
FIG. 8 is a diagrammatic view of a tubing set incorporating the cassette shown in FIGS. 5–7.

Inlet and outlet ports 60 and 61 are adapted to communicate with tubes 26 and 28 to produce a tubing set, preferably disposable, which may be used to communicate cooling fluid to and from handpiece 10. A representative example of such a tubing set is shown in FIG. 8 wherein cassette 30 has its inlet port 60 repositioned to the distal end of the cassette and its outlet port 61 situated at the proximal end of the cassette. In this example, tubing set 100 comprises an inflow tubing line 102 which has interposed along its length a pump cassette 104 for attaching the cassette to a peristaltic pump (not shown). At its distal end inflow line 102 is bifurcated into a motor cooling line 110 and a surgical-site cooling line 112, the distal end 114 of which is directed to cool a surgical tool driven by the handpiece. In the particular embodiment shown, the outflow of irrigation cassette 30 is directed to a drain tube 120 which may be made to drain directly into a waste receptacle (not shown). It will be understand that numerous variations of tubing set 100 may be made to incorporate the benefits of irrigation cassette 30 as well as providing other features. For example, drain tube 120 could be directed in order to recirculate fluid back to the fluid source from which inlet tube 102 receives coolant fluid so that a continual circulation loop could be produced which would continually flow coolant through the handpiece attached to irrigation cassette 30. This could be done with or without an in-line filter (not shown) and with or without a tube such as surgical site cooling tube 112. One advantage of such a recirculating loop is that the fluid used to cool the motor remains sterile and the fluid used to irrigate the surgical site is thus always sterile.

It will be understood by those skilled in the art that numerous improvements and modifications may be made to the preferred embodiment of the invention disclosed herein without departing from the spirit and scope thereof.

What is claimed is:

1. A fluid-cooled surgical handpiece system for use with a coolant source and coolant drain comprising:
   a body having a drive motor;
   a cooling chamber surrounding said motor for receiving coolant therein;
   a first inflow aperture for receiving said coolant from said coolant source and directing said coolant to said chamber;
   a first outflow aperture for directing said coolant from said chamber to said coolant drain;
   tubing set means for being engaged with said handpiece and for simultaneously engaging said inflow aperture and said outflow aperture and connecting them in fluid communication to said coolant source and said coolant drain, respectively; and
   means for securing said tubing set to said handpiece.

2. A fluid-cooled surgical handpiece system according to claim 1 wherein said handpiece comprises a first surface, wherein said inflow and outflow apertures are within the boundaries of said surface and wherein said tubing set means comprises a cassette for engagement with said handpiece, said cassette comprising:
   a second surface comprising a second inflow aperture and a second outflow aperture, said second surface adapted to engage a said first surface on said handpiece while placing said second inflow and outflow apertures in fluid communication with said first inflow and outflow apertures, respectively.

3. A fluid-cooled surgical handpiece system according to claim 2 wherein said cassette further comprises an exterior surface having a predetermined shape adapted to blend smoothly with the exterior surface of said handpiece adjacent said first surface.

4. A method of cooling a surgical handpiece having a drive motor and used at a surgical site comprising the steps of:
   providing a cooling chamber surrounding said drive motor;
   providing on said handpiece a first inflow aperture to receive cooling fluid and direct said coolant into said cooling chamber;
   providing on said handpiece a first outflow aperture to receive coolant from said cooling chamber and direct said coolant to a predetermined location;
   providing a tubing set comprising:
      a cassette having a second inflow aperture and a second outflow aperture;
      a first tubing means connected to said second inflow aperture for communicating fluid thereto; and
      a second tubing means connected to said second outflow aperture for communicating fluid thereto;
   securing said cassette to said handpiece to thereby operatively establish fluid communication between said second inflow and outflow apertures and said first inflow and outflow apertures, respectively; and
   flowing cooling fluid through said cooling chamber and said tubing set.

5. A method according to claim 4 further comprising the step of selectively attaching or detaching said cassette to said handpiece.

6. A method according to claim 4 further comprising the step of providing said tubing set with a third tubing means for communicating said cooling fluid directly to said surgical site.

* * * * *

UNITED STATES PATENT AND TRADEMARK OFFICE
CERTIFICATE OF CORRECTION

PATENT NO. : 6,171,300 B1
DATED : January 9, 2001
INVENTOR(S) : Kenneth M. Adams et al.

It is certified that error appears in the above-identified patent and that said Letters Patent is hereby corrected as shown below:

<u>Title Page,</u>
After Kenneth M. Adams, Tampa, FL (US) please add the following inventor
-- Brian J. Fox, St. Petersburg, FL (US) --

Signed and Sealed this

Ninth Day of October, 2001

Attest:

*Nicholas P. Godici*

NICHOLAS P. GODICI
*Attesting Officer*      *Acting Director of the United States Patent and Trademark Office*